United States Patent [19]
Reddy

[11] Patent Number: 4,797,289

[45] Date of Patent: Jan. 10, 1989

[54] ENHANCEMENT OF LACTOBACILLUS ACIDOPHILUS GROWTH AND VIABILITY IN YOGURT AND OTHER CULTURED DAIRY PRODUCTS

[76] Inventor: Malireddy S. Reddy, 6983 S. Telluride St., Aurora, Colo. 80016

[21] Appl. No.: 23,686

[22] Filed: Mar. 9, 1987

[51] Int. Cl.$^4$ .................. A23C 9/127; A23C 9/133
[52] U.S. Cl. .............................. 426/43; 426/583; 426/61
[58] Field of Search ............ 426/34, 42, 43, 61, 426/580, 583, 72–73, 74, 656–657

[56] References Cited

U.S. PATENT DOCUMENTS

| | | | |
|---|---|---|---|
| 3,025,164 | 3/1962 | Metzger | 426/43 |
| 3,080,236 | 3/1963 | Ferguson | 426/43 |
| 3,128,190 | 4/1964 | Donay et al. | 426/43 |
| 4,066,792 | 1/1978 | Kanda et al. | 426/43 |
| 4,410,549 | 10/1983 | Baker | 426/43 |

FOREIGN PATENT DOCUMENTS 3146198  5/1983  Fed. Rep. of Germany ........ 426/43

Primary Examiner—Marianne Cintins
Attorney, Agent, or Firm—Kyle W. Rost

[57] ABSTRACT

Lactobacillus acidophilus or bifidus does not grow and survive in yogurt for a long period of time. A differential inoculation procedure has been developed where by Lactobacillus acidophilus is first inoculated into heat treated milk or milk - sugar - fiber base and incubated until its population builds up sufficiently. Later, the regular yogurt cultures Streptococcus thermophilus and Lactobacillus bulgaricus are inoculated into the acidophilus growing yogurt mix. This procedure enables us to make yogurt with significantly high concentration of L. acidophilus bacteria in yogurt. Also dietetic fiber was introduced into the fruit base and then mixed with yogurt. Dietetic fiber we have employed not only benefits the health of the consumers, but also enhances the population of L. acidophilus. The fiber also thickens the yogurt due to its exceptional hydration properties. Vitamins and minerals are also included into the yogurt both to enhance the population of acidophilus and to supplement the yogurt. Variations of using lactase enzyme to decrease the lactose in yogurt and to enhance the L. acidophilus counts have been employed. In addition, to significantly prolong the viability of L. acidophilus, calcium carbonate and catalase-L have been included in the yogurt.

33 Claims, No Drawings

4,797,289

ENHANCEMENT OF LACTOBACILLUS ACIDOPHILUS GROWTH AND VIABILITY IN YOGURT AND OTHER CULTURED DAIRY PRODUCTS

BACKGROUND OF THE INVENTION

1. Field of the Invention

The invention relates to the development of a new yogurt product with significantly increased number of Lactobacillus acidophilus organisms along with usual number of Lactobacillus bulgaricus and Streptococcus thermophilus. The new yogurt also has dietetic fiber or food fiber, calcium carbonate, vitamins A, D, E, and C, along with high viable population of Lactobacillus acidophilus.

2. Description of the Prior Art

Yogurt is a fermented dairy product manufactured by fermenting milk with the aid of Lactobacillus bulgaricus and Streptococcus thermophilus. A brief dscreption of commercial yogurt manufacture is as follows:

1. Whole milk or partially skimmed milk fortified with nonfat dry milk (up to 3%) is pasteurized or heat treated and then cooled to 100° to 110° F.

2. The heat treated milk is inoculated with coccus (Streptococcus thermophilus), and rod (Lactobacillus bulgaricus) culture. Preferably, the coccus to rod ratio of the culture prior to inoculation is 1:1. Also, most generally the starter culture used is a frozen concentrate purchased from a commercial source. In some commercial preparation plants, a bulk starter medium is prepared by reconstituting nonfat dry milk solids in water, heating to 190° F. for 1 h, cooling to 100° to 110° F., and inoculating coccus and rod frozen culture. The medium is incubated until pH drops to from 4.2 to 4.5 and then cooled to 40° to 45° F. This bulk culture is inoculated into yogurt mix at the rate of 1 to 2%.

3. The coccus and rod inoculated mix is incubated at 100° to 113° F. until pH drops from 6.6 to 6.0. At this stage, the yogurt mix is pumped into a dispenser and it is dispensed into a cup with fruit preserve at the bottom.

4. The cups are selaed and moved into a warm room (100 to 114° F.) and held until pH drops to 4.8. Then the cups are placed in a cooler until the yogurt is cooled to 40° F. By then the pH of the final product is 4.0 to 4.4.

Whenever Swiss style type of yogurt is manufactured, the yogurt mix at pH 4.4 to 5.2 is mixed with the fruits and then it is filled into cups. Each manufacturer may have its own variations in making this yogurt.

Some of the manufacturers use Lactobacillus acidophilus or Lactobacillus bifidus along with the regular yogurt starter cultures, i.e. coccus (Streptococcus thermophilus) and rod (Lactobacillus bulgaricus). In this case, Lactobacillus acidophilus or L. bifidus is inoculated into the yogurt mix along with the regular yogurt cultures. The rate of growth of the yogurt cultures, coccus and rods, is much faster than that of L. acidophilus or L. bifidus. Consequently L. acidophilus or L. bifidus may not develop to a significant population. We have checked several commercial yogurts where L. acidophilus or L. bifidus initially was included and we could not detect significant number of L. acidophilus or bifidus bacteria. Even though the L. acidophilus or L. bifidus culture is added into yogurt mix, along with the regular yogurt cultures, the fate of the L. acidophilus is unknown. Perhaps L. acidophilus or bifidus cannot compete with the regular yogurt cultures. Consequently no one can make a deliberate statement with regard to acidophilus yogurt.

Literature documents the helpful, beneficial aspects of the L. acidophilus in the human being. They are:

1. Reduction of color cancer.
2. Reduction of intestinal flatulence.
3. Increased water retention in the gastrointestinal tract.
4. Reduction of cholesterol uptake into the blood stream.
5. Reduction of lactose intolerance.
6. Reduction of putrefactive and pathogenic bacterial population in the human gastrointestinal tract.

Thus far a successful way of including the L. acidophilus into human food has been in the form of "sweet acidophilus milk," where concentrated acidophilus bacterial culture is added to the cold fluid milk and then stored in the refrigerator. Such a milk most generally should have an L. acidophilus population of two million viable organisms per milliliter. Under acidic conditions (pH 3.0 to 4.0), L. acidophilus may not maintain its viability. Consequently, the latest fad is adding this organism to the fluid cold milk (pH 6.5 to 6.7).

It has been conclusively proven that a dietary fiber or food fiber included in the human diet has a pronounced effect on reducing colon cancer in human beings. In addition, it also has been claimed that fiber foods contribute to prevention of the following conditions: (1) constipation; (2) spastic colon; (3) intestinal diverticulosis; (4) varicose veins; and (5) excess cholesterol. Recently it also has been documented that high red meat consumption is increasing the incidence of colon cancer. This is because of the toxic end products formed in the gastrointestinal tract. Dietetic fiber increases the water retention in the gastrointestinal tract and thus reduces and dilutes the concentration of carcinogens in the intestinal tract. So far none of the dairy foods have significant amount of dietetic fiber included in them. Fruit base yogurts may have a slight amount of fiber if fresh fruits are included with skins. However most of the fruits are included with no skins and also in the form of puree.

Previous literature clearly states that L. acidophilus does not survive for a long period in yogurt. There also have been claims in literature regarding cancer retardation properties of vitamins A, E, and C. Further, vitamins C and E have an antioxidation effect, and consequently they may prolong the viability of the microorganisms during storage.

SUMMARY OF THE INVENTION

The primary object of the present invention is to enhance the growth of Lactobacillus Acidophilus and/or Lactobacillus bifidus in yogurt in relation to the regular yogurt organisms, Streptococcus thermophilus and Lactobacillus bulgaricus, through a different manufacturing procedure.

It is another object to retain and improve the viability of the Lactobacillus acidophilus and/or L. bifidus organisms in the yogurt and, thus, the implantational ability in the gastrointestinal tract.

It is another object to include dietary fiber into yogurt and other dairy fermented foods to enhance the growth of L. acidophilus and, thus, to obtain the benefits that may follow.

Another object is to add vitamins C & E and minerals to the yogurt as a supplement to the diet and, also, to improve the viability of *L. acidophilus* over a long period of time.

It is another object to include calcium carbonate into the yogurt to improve the viability of *L. acidophilus* over a long period of time and also to improve the texture and nutritional properties of the yogurt.

According to the invention, a method of making a cultured dairy product having a substantial quantity of viable *Lactobacillus acidophilus* micro-organisms includes the following steps. A base mixture that includes milk as a primary ingredient is prepared. The base mixture is pasteurized or otherwise heat treated and then cooled. The cooled base mixture is inoculated with a culture of *Lactobacillus acidophilus* to produce an acidophilus growing mixture. The acidophilus growing mixture is incubated to produce a substantial quantity of viable *Lactobacillus acidophilus* therein. Subsequently the acidophilus growing mixture is inoculated with a starter culture specific to the desired cultured dairy product to produce a dairy product mix. The dairy product mix is then incubated to produce a cultured dairy product having a substantial viable content of *Lactobacillus acidophilus*.

DESCRIPTION OF THE PREFERRED EMBODIMENTS

A cultured dairy product such as yogurt, buttermilk, cream cheese, or sour cream has been prepared by differential inoculation, first with a preferred bacteria such as *L. acidophilus*. After incubation of the base mixture, the traditional starter culture is added and further incubated to produce the desired cultured dairy product.

The base mixture is milk-based, consisting of cream, whole milk, nonfat dry milk, partially skimmed milk, skim milk, and reconstituted nonfat nonfat dry milk, or some combination of these milks. Milk fat may be added, especially for production of cream cheese or sour cream. A sugar such as fructose often is added to produce yogurt. High fructose corn syrup is a suitable source of fructose and may contain, for example, 5% to 20% of 25% to 60% solids fructose.

Certain modifications to the finished product have been developed. Especially, it is significant that dietary fiber, multi-vitamins, multi-minerals, calcium carbonate, and catalase-L have been incorporated into the finished product. Surpisingly, some of these additions have resulted in enhancement of the basic objective, benefiting the viability of *L. acidophilus*. Other of the additions have been achieved with continued good quality of the finished product. Most of the developmental work was done with yogurt as the most widely consumed representative of the class of cultured dairy products.

The yogurt has been prepared by using a yogurt base mixture of whole milk or partially skimmed milk with (3%) or without nonfat dry milk fortification along with 10.0% addition of 45 to 55% solids fructose sugar. The yogurt base mixture was pasteurized or heat treated at 160° to 190° F., preferably 180° F., for from one minute to forty-five minutes, preferably for 15 min. to 1 h, most preferably for 30 min., and it then is cooled to 95° to 115° F., preferably to 100° to 110° F.

At this stage, the bae mixture is inoculated with an active culture of *Lactobacillus acidophilus* to produce an acidophilus growing mixture. The *L. acidophilus* previously was grown in 12.0% reconstituted sterile nonfat dry milk or grown in phosphate whey base and/or milk base media or a frozen concentrate or an active lyophilized preparation. This single strain or a mixed strain of *Lactobacillus acidophilus* is incubated at 100° to 110° F. until pH of the mix came down to 6.0 to 6.3, preferably 6.0 to 6.2. This generally takes about 2 to 4 h. At this stage, a mixture of coccus and rod culture was added to the already growing *L. acidophilus* yogurt mix. The coccus to rod ratio at this stage was from 1–15:1, preferably 3:1. We found that if 1:1 coccus to rod ratio was used, the resultant yogurt had harsh acidic flavor. On the contrary, if 3–10:1 ratio was used, the resultant yogurt was normal and has a good flavor. However, if the coccus to rod ratio was from more than 20 to more than 100:1, the resultant yogurt was inferior in flavor.

The coccus and rod culture was prepared prior to inoculation by growing either in 12.0% reconstituted nonfat dry milk or 7.0% solids whey and nonfat base phosphated media. The coccus to rod ratios were adjusted by raising or lowering the set temperature of the starter culture. By raising the set temperature we have decreased the number of coccus in relation to the total number of rods. By lowering the set temperature, we were able to increase the number of coccus in relationship to number of rods in the starter medium. Under certain conditions a direct inoculation of frozen concentrated culture or concentrated lyophilized coccus and rod culture was used to inoculate the yogurt mix. The yogurt mix is then incubated at 100° to 110° F. until pH dropped to 5.6 to 6.1, preferably to 5.9 to 6.0, and then it is dispensed into a cup with fruit puree and flavor at the bottom.

Also, high fiber readily dispersible material, such as a dried or liquid dietary fiber, is added to the base mixture at the preferred rate of 0.1 to 3.0% by weight. A fiber content in the base mixture of as much as 20% may be suitable, although when the concentration of fiber exceeded 0.5%, it had a tendency to settle to the bottom of the container. Fiber also was added to the fruit puree, which in some instances was mixed with the finished yogurt to produce a fruit flavored yogurt. Certain fruit purees may contain natural fiber from the fruit. When the fruit base is non-fiber fortified, the fiber content is in the approximate range of from 0 to 0.1 percent pure dietary fiber.

The fruit puree and flavor was 10% to 30% of the entire contents of the mix, preferably 15% to 20% by weight. Also 5.0% to 30%, preferably 10% to 15% by weight, of the fruit puree was made of dietetic fiber, whichs of apple, pear or any other vegetable origin.

The yogurt mix plus the fiber fortified fruit puree was further incubated in a air incubator at 100° to 110° F. until pH of the mix was 4.8, and was cooled to 40° F. in a cooler. The final pH of the yogurt at the end of cooling was 3.8 to 4.6.

To make a Swiss style yogurt, first the yogurt mix was inoculated with *L. acidophilus*, and when the pH is down to 6.2, *L. bulgaricus* and *S. thermophilus* were added and allowed to incubate until pH came down to 4.6 to 5.0, preferably 4.8. The resultant yogurt product was cooled partially and then it was mixed with fiber-fortified fruit puree or fiber and calcium carbonate fortified fruit puree or fiber, calcium carbonate and catalase-L fortified fruit puree. The total fiber fruit or fiber and calcium carbonate fruit puree or fiber, calcium carbonate and catalase-L fortified fruit puree mixed yogurt is then dispensed into cups and cooled to 40° F. in a cooler. Here also, the final pH of the product is 3.8 to 4.6.

This yogurt can also be prepared by not including fiber in the yogurt mix and also in the fruit puree. In some cases, the yogurt was fortified with vitamins A, D, C, and E, along with other minerals. The yogurt thus prepared can be saved until 6 to 8 weeks at 40° F. The resultant yogurt was very high in active *L. acidophilus* organisms and, also, it supplies dietetic fiber without altering the texture and flavor of the yogurt. In addition to the benefits of *L. acidophilus* and fiber, the healthful aspects of the regular yogurt also can be derived.

Overall, this invention is unique in that the *L. acidophilus* and/or *L. bifidus* first is grown by itself in a base mixture (milk-fructose) until pH comes down to 6.2, and then the regular yogurt culture is added. By doing this, we have eliminated the dominating power of the regular yogurt cultures on *L. acidophilus* or *L. bifidus*. Consequently the population of *L. adicophilus* or *L. bifidus* was greatly improved. From our trials, it appears that the growth of *L. acidophilus* or *L. bifidus* was greatly improved because of the stimulatory effect of the fructose sugar added to the milk. Whenever the *L. acidophilus* or *L. bifidus* yogurt cultures were inoculated at the same time as the regular yogurt cultures, the total bacterial counts of *L. acidophilus* or *L. bifidus* were greatly decreased.

Accidentally, we also found that the apple fiber added to the yogurt mix significantly improved *L. acidophilus* or *L. bifidus* bacterial growth. This is rather unexpected. The logical explanation that can be offered is that an unknown simulatory compound is present in the apple fiber. Also, we have discovered that acid injury to the *L. acidophilus* or *L. bifidus* was greatly reduced when calcium carbonate was incorporated into the body of the yogurt to raise the pH. A concentration of from one to twenty percent by weight of calcium carbonate may be used.

The method of the present invention is further illustrated by the following examples.

EXAMPLE 1

A base mixture was prepared from 900 ml. whole milk, which was fortified with 24 grams of low heat nonfat dry milk. The addition of milk powder into cold, whole milk was accompanied by blending. To this mixture, 100 grams of 45% high fructose corn syrup was added. The entire resulting base mixture was heat treated at 180° F. and held at that temperature for 30 min. The mixture was cooled to 104° F., and the cooled base mixture was inoculated with milk-grown *Lactobacillus acidophilus* culture at the rate of 2.0% by weight to produce an acidophilus growing mixture. Then the acidophilus growing mixture was incubated until pH dropped to 6.2. It took roughly about 2 to 2½ h. At this stage a coccus and rod yogurt starter culture (grown in whey and nonfat dry milk base phosphated media) was added at the rate of 1.5% by weight to produce a yogurt mix, and was incubated until pH dropped 4.8, thus producing a yogurt product. Then the container as transferred into a refrigerator. When the contents were cooled to 40° F., the pH of the yogurt was 4.3. A similar experiment (as outlined above) was conducted using *Lactobacillus bifidus* organism in the place of *L. acidophilus*. Also, as another variable, *L. bifidus* and *L. acidophilus* were used in equal quantities and were inoculated in the place of *L. acidophilus*.

A set where we inoculated *Lactobacillus acidophilus* (2%) and coccus and rods (1.5%) at the same time served as a control. This mixture was also incubated at 104° F. It took only 4.0 h to get to pH 4.8. At this stage it was cooled by letting it sit in the refrigerator.

The *Lactobacillus acidophilus* counts were determined at several times, including right after adding the acidophilus culture into the yogurt mix; when the pH reached to 6.2 (prior to adding coccus and rod culture); and when the yogurt has been cooled to 40° F. or when the pH of the final product was 4.3. In the case of the control, *L. acidophilus* counts were determined at the time of inoculation (along with coccus and rods), and finally when the yogurt was cooled to 40° F. or when the pH was 4.3.

Lactobacillus counts were selectively determined by using MRS lactobacillus agar with 0.15% bile salts. The yogurt was serially diluted, plated, and was incubated at 37° C. for 48 h. The results of this experiment are presented in Table I.

It is quite clear from the data that *L. acidophilus* growth was significantly retarded when the *S. Thermophilus* and *L. bulgaricus* were present from the beginning of the growth. By differential inoculation, *L. acidophilus* counts were as good as the control, where no *S. thermophilus* or *L. bulgaricus* were present.

TABLE 1

| No. | Variable | *Lactobacillus acidophilus* counts/gm at: | | |
| --- | --- | --- | --- | --- |
| | | "0" time at at pH 6.6 | Later, at at pH 6.25 | at completion of making yogurt |
| 1. | *L. acidophilus* by itself, no coccus or rods added. | $6 \times 10^6$ | $80 \times 10^6$ | $120 \times 10^6$ |
| 2. | *L. acidophilus* and coccus and rods inoculated at the same time. | $5 \times 10^6$ | $5 \times 10^6$ | $17 \times 10^6$ |
| 3. | *L. Acidophilus* inoculated first, coccus and rods inoculated later at pH 6.25. | $4 \times 10^6$ | $72 \times 10^6$ | $130 \times 10^6$ |

EXAMPLE 2

900 ml. of whole milk was fortified with 24 grams of low heat nonfat dry milk. The addition of milk powder into whole milk was accomplished by blending. To this mixture 100 grams of 45% high fructose corn syrup and 10 grams of powdered apple dietary fiber was added. The apple dietary fiber in this and all other examples was a commercial preparation from Tree Top, Inc., P.O. Box 248, Selah, Wash. 98942. The entire base mixture was heat treated by heating and holding at 180° F. for 30 min. The base mixture was cooled to 104° F. and was inoculated with milk grown active *Lactobacillus acidophilus* culture, at the rate of 2.0%. Then, the resulting acidophilus growing mixture was incubated until pH dropped to 6.20. At this stage coccus and rod yogurt starter culture, (grown in whey and nonfat dry milk base phosphated media) was added at the rate of 1.5%, and the resulting yogurt mix was incubated until pH dropped to 4.8. Then the container was transferred into a refrigerator. When the yogurt was cooled to 40° F., the pH of the yogurt was 4.2.

A set where fiber was not added served as a control. The *L. acidophilus* counts were determined right after inoculation into the growing mixture, when the pH was down to 6.2 (prior to adding coccus and rod culture), and finally when the yogurt had pH 4.3 (after it is cooled to 40° F.). The results are presented in Table 2. The data indicate that the addition of fiber to yogurt base has a significant influence in promoting the growth of *L. acidophilus*.

TABLE 2

| | | Lactobacillus acidophilus counts/gm at: | | |
|---|---|---|---|---|
| No. | Variable | "0" time | Later, at at pH 6.25 | at completion of making yogurt |
| 1. | Diet fiber not added to yogurt base. | $3 \times 10^6$ | $80 \times 10^6$ | $140 \times 10^6$ |
| 2. | Diet fiber included in yogurt base before inoculation of *L. acidophilus* | $3 \times 10^6$ | $63 \times 10^6$ | $300 \times 10^6$ |

EXAMPLE 3

900 ml. of whole milk was fortified with 24 grams of low heat nonfat dry milk. The addition of milk powder into whole milk was accomplished by blending. To this mixture 100 grams of 55% high fructose corn syrup was added. The entire base mixture was heat treated by heating and holding at 180° F. for 30 min. The mixture was cooled to 104° F. and was inoculated with milk-grown active *Lactobacillus acidophilus* culture at the rate of 2.0%. Then, the resulting acidophilus growing mixture was incubated until pH dropped to 6.10. It took roughly about 2½ to 3 h.

At this stage coccus and rod starter culture (ratio of C:R was 1:1) was added at the rate of 1.5%, and was incubated until pH dropped to 5.8. Meanwhile, 10 grams of the dried apple fiber was mixed into 190 grams of fruit puree and this total of 200 grams was placed at the bottom of the sterile container. The fruit puree in this and all other examples was a commercial preparation from Lyons Magnus Co., Clovis, Calif. 800 ml. of the yogurt mix (pH 5.8) was dispensed on top of the puree and fiber mix and incubated at 104° F. until final pH came down to 4.8. At this stage, the entire 1000 grams of yogurt was placed in a refrigerator until it was cooled to 40° F. The following day it was evaluated for flavor, texture, and total acidophilus counts. A sample with no fiber added to the fruit base served as a control. The results, presented in Table 3, indicate that there was no significant increase in *L. acidophilus* when fiber was present in the fruit base rather than in the body of the yogurt.

TABLE 3

| | | Lactobacillus acidophilus counts/gm at: | | Flavor and Texture Evaluation: | | | |
|---|---|---|---|---|---|---|---|
| No. | Variable | "0" time | At completion of making yogurt | Flavor | Graininess | Body before mixing fruit | Body and visual appearance after mixing fruit |
| 1. | Fiber included in fruit base | $18 \times 10^6$ | $150 \times 10^6$ | Excellent | Slight graininess due to fiber | Firm custard type | Thick gel with colored fiber granules |
| 2. | Fiber not included in fruit base | $18 \times 10^6$ | $140 \times 10^6$ | Excellent | No graininess | Firm custard type | Thin gel with no colored granules |

EXAMPLE 4

900 ml. of whole milk was fortified with 24 grams of low heat nonfat dry milk. The addition of milk power into whole milk was accomplished by blending. To this mixture, 100 grams of 55% high fructose corn syrup and 1 gram of powdered apple dietetic fiber was added. The entire mixture as heat treated by heating and holding at 180° F. for 30 min. The mixture was cooled to 104° F. and was inoculated with milk grown active *Lactobacillus acidophilus* culture at the rate of 2.0% Then, it was incubated until pH dropped to 6.0. At this stage coccus and rod culture (coccus to rod ratio 3:1) was added at the rate of 1.5% and was incubated until pH dropped to 5.7. Meanwhile, 9 grams of the dried apple fiber was mixed into 191 grams of fruit puree and this total of 200 grams was placed at the bottom of the sterile container. 800 ml. of the yogurt mix (pH 5.8) was dispensed on top of the puree and fiber mix and incubated at 104° F. until pH came down to 4.3. Then, it was instantly cooled to 40° F. Yogurt base with no fiber added prior to inoculating *L. acidophilus* serve as a control. The following day, the yogurt products were evaluated for flavor, texture, and the total *L. acidophilus* bacterial counts. The results presented in Table 4 prove that the inclusion of the fiber in the body of the yogurt, prior to inoculation of *L. acidophilus*, were far superior to adding fiber to the fruit base only. It is preferable to add fiber to both the body of the yogurt and also to the fruit base.

TABLE 4

| | | Lactobacillus acidophilus counts/gm at: | | Flavor and Texture Evaluation: | | | |
|---|---|---|---|---|---|---|---|
| No. | Variable | "0" time | At completion of making yogurt | Flavor | Graininess | Body before mixing fruit | Body and visual appearance after mixing fruit |
| 1. | Fiber included both in yogurt base prior to inoculating *L. acidophilus* and in fruit base. | $20 \times 10^6$ | $380 \times 10^6$ | Typical | Slightly grainy | Very firm custard | Very thick gel with fiber granules |
| 2. | Fiber not included in yogurt base but included | $18 \times 10^6$ | $180 \times 10^6$ | Typical | Slightly grainy | Slightly firm custard | Slightly thick gel with fiber granules |

TABLE 4-continued

| No. | Variable | Lactobacillus acidophilus counts/gm at: | | Flavor and Texture Evaluation: | | | |
|---|---|---|---|---|---|---|---|
| | | "0" time | At completion of making yogurt | Flavor | Graininess | Body before mixing fruit | Body and visual appearance after mixing fruit |
| | in fruit base | | | | | | |

EXAMPLE 5

900 ml. of the whole milk was fortified with 24 grams of low heat nonfat dry milk. The addition of milk powder into whole milk was accomplished by blending. To this mixture, 100 grams of 55% high fructose corn syrup and 1 gram of powdered apple dietetic fiber was added. The entire mix was heat treated by heating and holding at 180° F. for 30 min. The mixture was cooled to 104° F. and was inoculated with active frozen concentrated Lactobacillus acidophilus culture. Then, it was incubated until pH dropped to 6.0.

At this stage coccus and rod culture (coccus to rod ratio 3:1) was added at the rate of 1.5% and was incubated until pH dropped to 4.3. The reslting yogurt was cooled to 40° F. to 50° F. Meanwhile 9 grams of the dried apple fiber was mixed into 191 grams of fruit puree and this fruit and fiber mixture was mixed with the yogurt mix until it was homogeneous. This constituted a flavored Swiss type yogurt. This yogurt was evaluated for flavor, texture and total *L. acidophilus* bacterial counts. A sample with fiber included in the fruit base but not stirred into the yogurt (sundae style) served as a control. The results presented in Table 5 indicate that the Swiss style, fiber fortified yogurt tends to enhance the *L. acidophilus* count over the sundae style fiber fortified yogurt.

TABLE 5

| No. | Variable | Lactobacillus acidophilus counts/gm at: | | Flavor and Texture Evaluation: | | |
|---|---|---|---|---|---|---|
| | | "0" time | At completion of making yogurt | Flavor | Graininess | Body after mixing fruit |
| 1. | Fiber mixed with fruit base & stirred with yogurt prior to final cooling (Swiss style) | $13 \times 10^6$ | $400 \times 10^6$ | Typical | Slight graininess but no syneresis | Slightly thick custard |
| 2. | Fiber mixed with fruit base but not stirred with yogurt prior to cooling (sundae style) | $115 \times 10^6$ | $330 \times 10^6$ | Typical | No graininess before mixing fruit puree. After mixing, slightly grainy. | Very thick custard |

EXAMPLE 6

900 ml. of the whole milk was fortified with 24 grams of low heat nonfat dry milk. The addition of milk powder into whole milk was accomplished by blending. To this mixture, 100 grams of 42% high fructose corn syrup was added. The entire mix was heat treated by heating and holding at 190° F. for 30 min. The mixture was cooled to 104° F. and was inoculated with active *L. acidophilus* culture, grown in whey and nonfat base phosphated media, at the rate of 2.0%. Then it was incubated until pH dropped to 6.2. At this stage coccus and rod culture (coccus to rod ratio 5:1) was added at the rate of 1.5% and was incubated until pH dropped to 4.5. This mixture was cooled to 45° F.

Meanwhile 10 grams of the dried pear fiber was mixed into 190 grams of fruit puree, and this fruit fiber mixture was mixed with the yogurt mix until it was homogeneous. This constituted a flavored Swiss type yogurt. The pear dietary fiber was a commercial preparation from Tree Top, Inc., P.O. Box 248, Selah, Wash. 98942. The yogurt was evaluated for flavor, texture and total *L. acidophilus* bacterial counts. A similar experiment with substitution of apple fiber served as a control. The results, presented in Table 6, prove that apple fiber as slightly superior to pear fiber in enhancing the *L. acidophilus* counts.

TABLE 6

| No. | Variable | Body | Texture | Flavor | L. acidophilus count/gm in the finished product. |
|---|---|---|---|---|---|
| 1. | Pear fiber included in the fruit base | Firm custard type body | Extremely grainy after mixing fruit with yogurt | Typical | $120 \times 10^6$ |
| 2. | Apple fiber included in fruit base. | Firm custard type body | Slightly grainy after mixing fruit with yogurt. | Typical | $160 \times 10^6$ |

EXAMPLE 7

900 ml. of skim milk was fortified with 24 grams of nonfat dry milk powder. The addition of milk powder was accomplished by blending. To this mixture was added 100 grams of 52% high fructose corn syrum and 1 gram of dried apple fiber. The entire base mix was heat treated by heating and holding at 190° F. for 30 min. The mixture was cooled to 104° F. and was inoculated with active *L. acidophilus* culture. Then it was incubated until pH dropped to 6.2. At this stage coccus and rod culture (coccus to rod ratio 5:1) was added at the rate of 1.5% and was incubated until pH dropped to 6.0. 450 ml. of the mixture at pH 6.0 was transferred to a container that has fruit and fiber mix (fruit puree 95 grams and apple fiber 4.5 grams) at the bottom. This container was further incubated until pH dropped to 4.8 and was cooled slowly to 40° F.

The remainder of the 450 ml. of yogurt mix was allowed to incubate at 104° F. until pH dropped to 4.3 and then it was mixed with fruit and fiber mix (fruit puree 95 grams and apple fiber 4.5 grams). The entire mix was quickly cooled to 40° F.

Thus, in this example, both the Swiss style and sundae style yogurts were prepared using skim milk as a base. Both styles of yogurt were evaluated for flavor, texture, and total acidophilus bacterial counts. The results are presented in Table 7. According to the data, the Swiss style fiber fortified nonfat yogurt was slightly superior to sundae style fiber fortified nonfat yogurt, in terms of promoting *L. acidophilus* counts.

TABLE 7

| No. | Variable | Body | Texture | Flavor | *L. acidophilus* count/gm in the finished product. |
|---|---|---|---|---|---|
| 1. | Nonfat yogurt mixed with fiber-fruit base | Custard body | Extremely grainy due to lack of fat. | Typical | $380 \times 10^6$ |
| 2. | Nonfat yogurt placed on top of fiber-fruit base (Sunday style) | Custard body | Extremely grainy due to lack of fat. | Typical | $350 \times 10^6$ |

EXAMPLE 8

To make a thin bodied, drinkable yogurt, 100 grams of the 52% fructose corn syrup was added 900 ml. of the 2.2% skim milk. The entire mix was divided into two 500 ml. fractions. To one 500 ml. fraction, 0.5 grams of the dried apple fiber was added. To the remaining 500 ml. fraction, fiber was not added. Both the fractions were heat treated by heating and holding at 180° F. for 30 min. They were cooled to 104° F. and inoculated with active *L. acidophilus* culture. After the pH of the mixture dropped to 6.2., active yogurt culture was inoculated and it was further incubated until pH dropped to 5.0. At this stage the two fractions were each subdivided to produce four fractions in two groups. To one fraction of each group, 250 grams of fruit puree with fiber was added (fruit puree 47.5 grams and apple fiber 2.25 grams). To the other fraction from each group, only fruit puree (49.75 grams) was added. After mixing all the ingredients the yogurt was cooled to 40° F. and evaluated using organoleptic analysis. The results are presented in Table 8.

TABLE 8

| | | *Lactobacillus acidophilus* counts/gm at: | | Flavor and Texture Evaluation | | | |
|---|---|---|---|---|---|---|---|
| No. | Variable | "0" time | At completion of making yogurt | Body | Graininess | Flavor | Syneresis |
| 1. | Fiber added to yogurt mix, then fruit puree with fiber blended at pH 5.0 | $8 \times 10^6$ | $150 \times 10^6$ | Thick bodied liquid | Slightly grainy | Mild yogurt flavor | None |
| 2. | Fiber added to yogurt mix, then fruit puree with no fiber blended at pH 5.0 | $8 \times 10^6$ | $130 \times 10^6$ | Thin bodied liquid | Slightly grainy | Mild yogurt flavor | Slight |
| 3. | No fiber added to yogurt mix, then fruit puree with fiber blended at pH 5.0 | $8 \times 10^6$ | $100 \times 10^6$ | Partially thick bodied liquid | Slightly grainy | Very mild yogurt yogurt flavor | None |
| 4. | No fiber added to yogurt mix, then fruit puree with no fiber added | $8 \times 10^6$ | $86 \times 10^6$ | Thin bodied liquid | No graininess at all | Very mild yogurt flavor | Slight |

EXAMPLE 9

The following experiment was conducted to break the lactose sugar present in the milk, using lactase enzyme and then making yogurt using our differential inoculation procedure. After fortifying whole. milk (2000 ml) with 4% of nonfat dry milk, the resulting fortified milk was divided into two fractions. To the first fraction, 42% high fructose sugar was added at the rate of 10.0%. No fructose was added to the second fraction. The two base mixtures were heat treated to 180° F. for 30 min. and then cooled to 104° F.

Then, each of the two fractions was subdivided into a group of two equal portions. An appropriate amount of lactose (0.01%) was added to one member of each group. Simultaneously, *L. acidophilus* was inoculated into both the lactase added and non-lactase added mixtures of both groups. Following incubation, pH dropped to 6.1 to 6.2. Then, the mixtures were inoculated with coccus and rod cultures and incubated until pH dropped to 5.8. At this stage the mixtures were dispensed into cups with fiber-fortified fruit base at the bottom. All these mixtures were incubated until pH of the final mix was down to 4.8 to 5.0, after which they were cooled to 40° F. in a refrigerator. The final pH of the product after cooling was 4.2 to 4.4. All the combinations, i.e., with and without lactase treatment, were analyzed for texture, sweetness, flavor, and *L. acidophilus* counts. The results are presented in Table 9. The results indicate that the lactase treatment seems to enhance *L. acidophilus* counts. This probably is due to the availability of simple sugars.

TABLE 9

| No. | Variable | *Lactobacillus acidophilus* counts/gm at: | | Flavor and Texture Evaluation | | |
|---|---|---|---|---|---|---|
| | | "0" time | At completion of making yogurt | Body | Sweetness | Graininess |
| 1. | Lactase treated with fructose addition | $2 \times 10^6$ | $180 \times 10^6$ | Very firm | Maximum sweetness | Slight |
| 2. | No lactase treatment, with fructose addition | $2 \times 10^6$ | $150 \times 10^6$ | Firm | Average sweetness | Slight |
| 3. | Lactase treated with no fructose addition | $2 \times 10^6$ | $140 \times 10^6$ | Slightly weak | Slight sweetness before adding puree | Slight |
| 4. | No lactase treatment with no fructose fortification | $2 \times 10^6$ | $92 \times 10^6$ | Distinctly weak | No sweetness before adding puree | Slight |

EXAMPLE 10

To check the effect of length of storage on the viability of *Lactobacillus acidophilus*, the yogurt was subjected to storage for a period of eight weeks. The yogurt was prepared using our differential inoculation procedure as described in the above examples, both with and without fiber fortification. The *L. acidophilus* counts were determined at the end of making, two days, one week, six weeks, and eight weeks later. The storage temperature selected for yogurt as 4° C. The results are presented in Table 10. It is clear from the data that even though fiber enhanced the growth of *L. acidophilus*, with storage the counts decreased at the end of three weeks.

TABLE 10

| No. | Variable | *Lactobacillus acidophilus* counts/gm. at: | | | | | |
|---|---|---|---|---|---|---|---|
| | | The end of make | 24 hours later | 1 week | 3 weeks | 6 weeks | 8 weeks |
| 1. | Fiber not included in yogurt mix | $150 \times 10^6$ | $130 \times 10^6$ | $120 \times 10^6$ | $20 \times 10^6$ | $5 \times 10^6$ | $3 \times 10^6$ |
| 2. | Fiber included in yogurt mix | $360 \times 10^6$ | $380 \times 10^6$ | $300 \times 10^6$ | $90 \times 10^6$ | $10 \times 10^6$ | $7 \times 10^6$ |

EXAMPLE 11

The effect of $CaCO_3$ on maintaining the viability of *L. acidophilus* upon storage was checked. The calcium carbonate in this and all other examples was obtained from Pfizer, Inc.; Minerals, Pigments, and Metals Division; New York, N.Y. 10017. After making the yogurt (pH 4.3) using our differential inoculation procedure as described in the above examples, food grade calcium carbonate was added to the yogurt (0.5 to 3%) with stirring to get the pH up to 4.5 to 5.1. The resultant yogurt with $CaCO_3$ added (pH 4.9), along with negative control (no $CaCO_3$) was stored at 4° C. for a period of eight weeks.

*Lactobacillus acidophilus* counts were determined at first day, second day, one week, six weeks, and eight weeks later. The results are presented in Table 11. Addition of calcium carbonate significantly increased the viability of *L. acidophilus* in yogurt during the period of storage.

TABLE 11

| No. | Variable | *Lactobacillus acidophilus* counts/gm. at: | | | | | |
|---|---|---|---|---|---|---|---|
| | | The end of make | 24 hours later | 1 week | 3 weeks | 6 weeks | 8 weeks |
| 1. | Fiber included in yogurt but no $CaCO_3$ added | $340 \times 10^6$ | $350 \times 10^6$ | $280 \times 10^6$ | $82 \times 10^6$ | $8 \times 10^6$ | $5 \times 10^6$ |
| 2. | Fiber plus $CaCO_3$ included in yogurt | $350 \times 10^6$ | $400 \times 10^6$ | $390 \times 10^6$ | $310 \times 10^6$ | $200 \times 10^6$ | $110 \times 10^6$ |

EXAMPLE 12

Yogurt was prepared according to the procedure outlined in example 11, with the following change: To the yogurt mix (without fruit puree) at pH 4.4, 0.1 to 1 percent of 1 in 100 dilution of commercial catalase-L preparation was added prior to adding calcium carbonate and the fruit puree. The enzyme, catalase-L, is supposed to destroy the microbial hydrogen peroxide, which is toxic to *L. acidophilus*. We ran a second experiment using catalase-L only, without using calcium carbonate.

After preparing the yogurts using our differential inoculation procedures to enhance *L. acidophilus*, with and without incorporation of catalase-L and calcium carbonate, the yogurts were analyzed for *L. acidophilus* counts for a period of two months. The results, presented in Table 12, indicate that either catalase-L alone or calcium carbonate alone were not superior in maintaining the *L. acidophilus* counts during storage when compared to the combined use of catalase-L and calcium carbonate at the time of cooling the yogurt. The use of calcium carbonate was far superior to the use of catalase-L in maintaining the viability of *L. acidophilus*. However, the use of catalase-L and calcium carbonate, added to the body of the yogurt either separately or in combination with fruit puree, significantly improved the viability of the *L. acidophilus* during storage of up to two months.

TABLE 12

| No. | Variable | *Lactobacillus acidophilus* counts/gm at: | | |
|---|---|---|---|---|
| | | 1st day | The end of at 1st month | The end of 2nd month |
| 1. | Only calcium carbonate added | $320 \times 10^6$ | $250 \times 10^6$ | $150 \times 10^6$ |
| 2. | Only catalase-L added | $320 \times 10^6$ | $160 \times 10^6$ | $85 \times 10^6$ |
| 3. | Calcium carbonate and catalase-L added | $320 \times 10^6$ | $290 \times 10^6$ | $230 \times 10^6$ |

EXAMPLE 13

The acidophilus and fiber based yogurt made using our differential inoculation procedure was fortified with 2000 to 4000 I.U. of vitamin A; 30 I.U. of vitamin E, and 20 to 60 mg. of vitamin C. The vitamins were obtained from Star Blends, Inc., St. Joseph, Mo. 64503. Another batch of yogurt was mixed with multi-vitamin powder and multi-mineral powder to supply the U.S.R.D.A. for every six ounce serving. The yogurts were analyzed organoleptically for body and flavor. The results indicated that the vitamin or mineral fortifications did not alter the body, texture, or flavor of the acidophilus yogurt.

EXAMPLE 14

Our differential inoculation procedure was adapted to make cultured buttermilk, sour cream and cream cheese. A traditional method of producing buttermilk is to heat whole milk or skim milk to 180° F. for ½ h.; cool the milk to 70° to 75° F.; inoculate with lactic culture; incubate until pH reaches 4.5; and cool to 40° F. A traditional method of producing sour cream is to start with cream that has been standardized to a 19% fat content; heat the standardized cream to 165° F. for ½ h and homogenize; cool to 110° F. and homogenize again; then cool to 72° to 75° F.; add lactic culture and incubate until pH drops to 4.5. A traditional method of producing cream cheese is to start with cream standardized to 11% fat content; heat to 155° F. for ½ h; cool to 120° F. and homogenize; cool to 72° to 75° F.; add lactic culture; incubate until ph drops to 4.5; break the curd; cook the curd; add salt; cool to 40° to 45° F.; place the cooled mass in bags; drain; and mix and package the resulting cheese.

These products were made using traditional manufacturing procedures, with the only difference being that *L. acidophilus* was grown first at high temperature (100° to 106° F.) until pH dropped to 6.1. Then the mixture was cooled to 72° to 78° F. and the lactic culture was used to bring the pH down to 4.4 to 4.8. Some sets of samples were neutralized with $CaCO_3$ and treated with catalase-L and others were not. All the products were compared with non-acidophilus and non-fiber added controls. The acidophilus based cultured products were fairly comparable to the negative controls in terms of flavor and body. Whenever fiber was included, with and without flavoring and with and without $CaCO_3$, slight graininess was observed.

I claim:

1. A method of making a cultured dairy product having a substantial quantity of viable *Lactobacillus acidophilus* micro-organisms, said method comprising the steps of:
   preparing a base mixture comprising milk;
   pasteurizing or heat treating said base mixture;
   cooling the base mixture;
   inoculating the cooled base mixture with a culture of *Lactobacillus acidophilus* in a quantity sufficient to drop the pH to within the range of 6.0 to 6.3 to produce an acidophilus growing mixture;
   incubating said acidophilus growing mixture until the pH drops wihtin the range of 6.0 to 6.3 to produce a substantial quantity of viable *Lactobacillus acidophilus* therein;
   subsequently inoculating the acidophilus growing mixture with a starter culture specific to the cultured dairy product to produce a dairy product mix; and
   incubating said dairy product mix to produce a cultured dairy product having a substantial viable content of *Lactobacillus acidophilus*.

2. The method of claim 1, wherein said milk of the base mixture comprises a milk selected from the group consisting of cream, whole milk, partially skimmed milk, skim milk, and reconstituted nonfat dry milk.

3. The method of claim 1, wherein said base mixture further comprises a sugar.

4. The method of claim 3, wherein said sugar in the base mixture comprises from 5% to 20% by weight of 25% to 60% solids fructose.

5. The method of claim 1, wherein said base mixture further comprises from 0 to 20.0 percent by weight dried or liquid dietary fiber.

6. The method of claim 5, wherein said dietary fiber has its origin from apple.

7. The method of claim 1, wherein in said step of cooling the heat treated base mixture, the base mixture is cooled to from 95° to 110° F.

8. The method of claim 1, wherein said cultured dairy product is yogurt, and said method further comprises, after the step of incubating said dairy product mix to produce yogurt:
   adding the yogurt to a fruit base to produce a fruit-flavored yogurt product.

9. The method of claim 8, wherein said fruit base is fiber fortified fruit base and comprises dietary fiber of from 5 to 30 percent by weight; and
   the yogurt is mixed with the fruit base.

10. The method of claim 8, wherein said fruit base is non-fiber fortified and comprises from 0 to 0.1 percent by weight dietary fiber; and
    the yogurt is mixed with the fruit base.

11. The method of claim 8, wherein said fruit base constitutes 10 to 30% by weight of the total flavored yogurt.

12. The method of claim 8, wherein said fruit base is fortified with vitamin A, vitamin C, vitamin D, and vitamin E.

13. The method of claim 8, wherein said fruit base is fortified with minerals.

14. The method of claim 8, wherein said fruit base further comprises calcium carbonate.

15. The method of claim 14, wherein the concentration of calcium carbonate is from approximately one to twenty percent by weight.

16. The method of claim 8, further comprising:
mixing said yogurt and fruit base to produce a fruit flavored yogurt product; and
neutralizing said yogurt product by adding calcium carbonate.

17. The method of claim 16, wherein calcium carbonate is added until the pH of the yogurt product is from about 3.8 to 5.8.

18. The method of claim 1, wherein said cultured dairy product is yogurt.

19. The method of claim 1, wherein said cultured dairy product is yogurt, and said starter culture specific to the cultured dairy product is active yogurt culture comprising *Streptococcus thermophilus* and *Lactobacillus bulgaricus* at pH 6.0 to 6.3.

20. The method of claim 1, wherein said cultured dairy product is yogurt;
said starter culture comprises *S. thermophilus* and *L. bulgaricus;* and
said dairy product mix is incubated at 100° to 110° F., until pH drops to from 5.0 to 4.6.

21. The method of claim 1, further comprising adding lactase enzyme to the said cooled base mixture.

22. The method of claim 1, further comprising adding calcium carbonate to said cultured dairy product.

23. The method of claim 22, wherein the concentration of calcium carbonate is from approximately 0.5% to 3.0% by weight.

24. The method of claim 22, wherein sufficient calcium carbonate is added to raise the pH of the cultured dairy product to approximately 4.9.

25. The method of claim 1, further comprising adding catalase-L enzyme to said cultured dairy product.

26. The method of claim 25, wherein the concentration of catalase-L enzyme is approximatey 0.1 to 1% by weight of 1 to 100 dilution catalase-L.

27. A method of making a culture dairy product having a 0.1 to 3.0 percent quantity of dietary fiber and a substantial quantity of viable *Lactobacillus acidophilus* microorganisms, said method comprising the steps of:
preparing a base mixture comprising milk and dietary fiber;
pasteurizing or heat treating said base mixture;
cooling the base mixture;
inoclutaing the cooled base mixture with a culture of *Lactobacillus acidophilus* in a quantity sufficient to drop the pH to within the range of 6.0 to 6.3 to produce an acidophilus growing mixture; incubating said acidophilus growing mixture until the pH drops within the range of 6.0 to 6.3 to produce a substantial quantity of viable *Lactobacillus acidophilus* therein; subsequently inoculating the acidophilus growing mixture with a starter culture specific to the culture dairy product to produce a dairy product mix; and
incubating said dairy product mix to produce a cultured dairy product having a 0.1 to 3.0 percent content of dietary fiber and a substantial viable content of *Lactobacillus acidophilus.*

28. The method of claim 27, wherein said dietary fiber is dried or liquid dietary fiber.

29. The method of claim 27, wherein said dietary fiber has its origin from apple.

30. The method of claim 27, wherein said cultured dairy product is yogurt, and said method further comprises, after the step of incubating said dairy product mix to produce yogurt:
adding the yogurt to a fruit base to produce a fruit-flavored yogurt product.

31. The method of claim 30, wherein said first base is fiber fortified fruit base and comprises dietary fiber of from 5 to 30 percent by weight; and
the yogurt is mixed with the fruit base.

32. The method of claim 30, wherein said fruit base is non-fiber fortified and comprises from 0 to 0.1 percent by weight dietary fiber; and
the yogurt is mixed with the fruit base.

33. The method of claim 30, wherein said fruit base constitutes 10 to 30 percent by weight of the total flavored yogurt.

* * * * *